United States Patent [19]

Junino et al.

[11] Patent Number: 5,114,429
[45] Date of Patent: May 19, 1992

[54] ALIPHATIC ALPHA, OMEGA-DIAMINE COMPOUNDS AND THEIR USE IN HAIR DYEING

[75] Inventors: Alex Junino, Livry-Gargan; Alain Genet, Aulnay-sous-Bois; Gérard Lang, Saint-Gratien, all of France

[73] Assignee: L'oreal, Paris, France

[21] Appl. No.: 403,390

[22] Filed: Sep. 6, 1989

[30] Foreign Application Priority Data

Sep. 6, 1988 [FR] France .................. 88 11634

[51] Int. Cl.$^5$ .................. A61K 7/13; C07C 211/51; C07C 211/55
[52] U.S. Cl. .................. 8/410; 8/406; 8/408; 8/411; 8/416; 564/305; 564/443
[58] Field of Search .................. 8/406, 410, 411, 416, 8/408; 564/305, 443

[56] References Cited

U.S. PATENT DOCUMENTS

| | | | |
|---|---|---|---|
| 1,210,751 | 1/1917 | Anderwert et al. | 564/305 |
| 3,694,138 | 9/1972 | Kalopissis et al. | 8/410 |
| 4,010,200 | 3/1977 | Kalopissis et al. | 8/416 |
| 4,137,080 | 1/1979 | Fujiwhara et al. | 96/55 |
| 4,211,561 | 7/1980 | Plambeck, Jr. | 430/306 |
| 4,314,809 | 2/1982 | Rose et al. | 8/406 |
| 4,629,466 | 12/1986 | Rose et al. | 8/416 |
| 4,842,612 | 6/1989 | Rose et al. | 8/416 |

FOREIGN PATENT DOCUMENTS 1266766 4/1968 Fed. Rep. of Germany .
1939062 4/1970 Fed. Rep. of Germany .

Primary Examiner—A. Lionel Clingman
Assistant Examiner—Linda D. Skaling
Attorney, Agent, or Firm—Fleit, Jacobson, Cohn, Price, Holman & Stern

[57] ABSTRACT

The invention relates to the new compounds consisting of N,N'-bis($\beta$-hydroxyethyl)-N,N'-bis(4'-aminophenyl)-1,3-diamino-2-propanol and N,N'-bis(ethyl)-N,N'-bis(4'-amino-3'-methylphenyl)ethylenediamine, and their use in keratinous fiber dyeing compositions and processes.

8 Claims, No Drawings

ALIPHATIC ALPHA, OMEGA-DIAMINE COMPOUNDS AND THEIR USE IN HAIR DYEING

The present invention relates to a new process for preparing N,N'-tetrasubstituted aliphatic α,δ-diamines, to the new compounds consisting of N,N'-bis(β-hydroxyethyl)-N,N'-bis(4'-aminophenyl)-1,3-diamino-2-propanol and to N,N'-bis(ethyl)-N,N'-bis(4'-amino-3'-methylphenyl)ethylenediamine, their addition salts with acids and their use in oxidation hair dyeing.

A process has already been described in French Patent 2,016,123 and U.S. Pat. No. 3,694,138 for preparing N,N'-diphenylalkylenediamines whose phenyl rings are para-substituted by an OH or amino group, this amino group being optionally substituted by an alkyl radical and it being possible for the amine groups themselves to be substituted by an alkyl, hydroxyalkyl or aminoalkyl group.

The process for preparing these compounds consists essentially in performing, in a first stage, a reaction of tosylation of p-acetaminoaniline to obtain N-acetyl-N'-tosyl-para-phenylenediamine, followed, in a second stage, by a condensation of a dihalohydrocarbon with an alkali metal or alkaline-earth metal salt of N-acetyl-N'-tosyl-para-phenylenediamine, in carrying out, in a third stage, a selective hydrolysis of the tosyl groups of the N,N'-bistosyl-N,N'-bis(4'-acetamidophenyl) alkylenediamine obtained during the second stage. This hydrolysis is carried out with the aid of cold sulphuric acid and produces N,N'-bis(4'-acetamidophenyl)alkylenediamine.

The fourth stage of this previous process is an alkylation or a hydroxyalkylation or aminoalkylation of the secondary amine functional groups.

Lastly, the fifth stage consists in performing the hydrolysis of the acetamido functional group by reaction with hydrochloric acid with heating.

This process has the disadvantage of being long and costly and difficult to implement industrially.

The Applicant has found, and this is what forms the subject-matter of the present invention, a new preparative process which is much simpler and faster and which makes use of commonly employed raw materials.

This process is represented by the reaction scheme A.

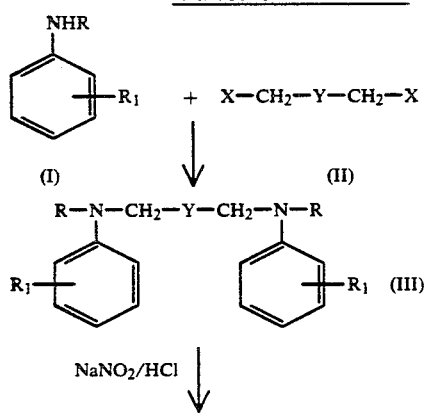

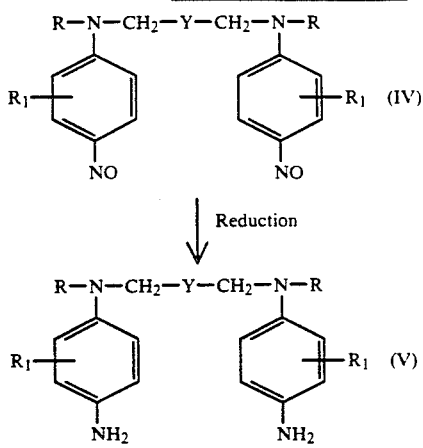

In the various abovementioned formulae (I), (II), (III), (IV) and (V), R denotes a $C_1$-$C_4$ alkyl, $C_2$-$C_4$ hydroxy alkyl or $C_2$-$C_4$ aminoalkyl radical, X denotes a halogen atom, preferably chlorine or bromine, $R_1$ denotes a hydrogen or halogen atom or a $C_1$-$C_4$ alkyl radical, Y denotes the group —$(CH_2)_n$—with n having a value from 0 to 8, or else the group —$(CH_2)_{n'}$—CHOH —$(CH_2)_n$—where $n'$ is an integer from 0 to 4.

The process for preparing the compounds of formula (V) or their salts, in accordance with the invention, is essentially characterized in that:

(1) a dihalogenated hydrocarbon of formula (II) is condensed with an N-substituted aniline (I) in a polar solvent and in the presence of a basic compound;

(2) the compound thus formed (III) is nitrosated; and (3) the nitroso derivative (IV) is reduced to obtain the compound of formula (V).

Stoichiometric quantities, or else a slight excess, of the dihalogenated hydrocarbon of formula (II) relative to the N-substituted aniline of formula (I), are preferably employed in the first stage of the process in accordance with the invention.

The polar solvent is preferably water. The basic compound is employed in sufficient quantities to trap the hydrogen halide acid formed and it is preferably chosen from alkali metal or alkaline-earth metal carbonates. The reaction temperature preferably varies between 50° C. and the reflux temperature of the reaction mixture.

The nitrosation reaction is carried out essentially by reaction with a sodium nitrite/hydrochloric acid mixture in water, at a temperature below 10° C., preferably between −2° and +5° C.

The reduction applied in the third stage of the process is performed in an ethanolic medium in the presence of ammonium chloride and zinc at the reflux temperature of the solvent.

The reduction can also be carried out by a catalytic route in a solvent consisting of a lower $C_1$-$C_4$ alcohol, a water-alcohol mixture, ethyl acetate or tetrahydrofuran, using nickel, platinum or palladium on charcoal as a catalyst The reduction can also be performed under hydrogen pressure at a temperature of between 20° C. and 100° C. and at a pressure which is preferably below 10 bars (1000 kPa).

The compounds of formula (IV) in which R denotes a $C_2$-$C_4$ hydroxyalkyl or $C_2$-$C_4$ aminoalkyl, $R_1$ and Y having the same meanings as above, are new and form another subject of the invention.

Another subject of the invention consists of N,N'-bis($\beta$-hydroxyethyl)-N,N'-bis(4'-aminophenyl) -1,3-diamino-2-propanol and of N,N'-bis(ethyl)-N,N'-bis(4'-amino-3'-methylphenyl) ethylenediamine and their addition salts with acids.

Another subject of the invention consists of the use of one or both of these new compounds or of their salts as an oxidation dye precursor of the para type in oxidation dyeing compositions for hair. These compounds produce dyes which are stable to washing, to light and to inclement weather, and are satisfactorily innocuous.

In the oxidation dye compositions for hair, the compound defined above may be employed in combination with tinters or couplers chosen, in particular, from phenols, meta-diphenols, meta-aminophenols, meta-phenylenediamines, mono- or polyhydroxylated derivatives of naphthalene and of aminonaphthalene, pyrazolones, benzomorpholines, heterocyclic couplers derived from pyridine, sesamol and its derivatives.

In the oxidation dye compositions the concentration of the dye precursor defined above is generally between 0.05 and 12% and preferably between 0.1 and 5% by weight. When present, couplers are employed in concentrations of between 0.05 and 10% by weight relative to the total weight of the composition.

The pH of these compositions is preferably alkaline and, in particular, it is between 8 and 11.

These compositions contain the dye precursor in a suitable medium for dyeing, known per se, which may be more or less thickened or jelled liquid, an emulsion, a foam or any other form which is suitable for dyeing.

This medium is preferably aqueous and may consist of water or a mixture of water and an organic solvent such as ethyl alcohol, propyl or isopropyl alcohol, tert-butyl alcohol, benzyl or phenylethyl alcohol, ethylene glycol, polyethylene glycols, ethylene glycol monomethyl, monoethyl or monobutyl ethers, ethylene glycol monoethyl ether acetate, propylene glycol, propylene glycol and dipropylene glycol monomethyl ethers or methyl lactate.

These compositions may contain any other adjuvant usually employed in dyeing keratinous fibres, in particular anionic, cationic, nonionic or amphoteric surface-active agents or mixtures thereof, thickening agents, perfumes, sequestering agents, film-forming agents, processing agents, dispersing agents, conditioning agents, preserving agents, opacifying agents, agents for swelling keratinous fibres, and the like.

The compositions in accordance with the invention may also contain direct dyes intended to tint the colour, such as the nitro derivatives of the benzene series and anthraquinone, naphthaquinone or azo dyes.

The process for dyeing keratinous fibres, in particular human hair, consists in applying to these fibres a composition containing at least one dye precursor defined above in a sufficient quantity to dye them. This composition is preferably mixed beforehand with an oxidizing agent such as hydrogen peroxide or a persalt, with a view to developing the colour.

The composition is kept in contact with the fibres for a period of 5 minutes to 1 hour and a rinsing is then carried out, followed optionally by washing, rinsing again and drying.

The examples which follow are intended to illustrate the invention without, however, being limiting in nature.

EXAMPLE OF PREPARATION 1

Preparation of N,N'-bis($\beta$-hydroxyethyl)-N,N'-bis(4'-aminophenyl)-1,3-diamino-2-propanol

1st stage:

Preparation of N,N'-bis($\beta$-hydroxyethyl)-N,N'-bis(phenyl)-1,3-diamino-2-propanol The mixture consisting of 2 moles (274.4 g) of N-$\beta$-hydroxyethylaniline, 140 g of calcium carbonate and 1.2 moles (154.8 g) of 1,3-dichloro-2-propanol in 1 litre of water is heated for 6 hours under water reflux.

The expected product crystallizes after cooling and neutralizing with 50 ml of concentrated hydrochloric acid.

After filtering off and washing with water, the product obtained is recrystallized from isopropyl alcohol. 238 g of the expected product are obtained. It melts at 120° C.

Analysis of the product obtained gives the following results:

Analysis for $C_{19}H_{26}N_2O_3$

|  | C % | H % | N % | O % |
| --- | --- | --- | --- | --- |
| Calculated | 69.06 | 7.93 | 8.48 | 14.53 |
| Found | 69.13 | 7.96 | 8.38 | 14.82 |

2nd stage:

Preparation of N,N'-bis($\beta$-hydroxyethyl)-N,N'-bis(4'-nitrosophenyl)-1,3-diamino-2-propanol A solution of 1.14 moles (78.7 g) of sodium nitrite in 150 ml of water is added dropwise at between 0° C. and 5° C. to a solution of 0.5 moles (165.2 g) of N,N'-bis($\beta$-hydroxyethyl)-N,N'-bis(phenyl) -1,3-diamino-2propanol, prepared in the preceding stage, 290 ml of concentrated hydrochloric acid and 900 g of ice. After the end of addition stirring is continued for 1 h 30 min. The reaction mixture is neutralized by adding 300 ml of 20% strength aqueous ammonia at 10° C. After filtering off, the product obtained is made into a paste with water. It can be employed moist for the following stage.

3rd stage

Preparation of N,N'-bis($\beta$-hydroxyethyl)-N,N'-bis[(4'-amino)phenyl]-1,3-diamino-2-propanol tetrahydrochloride hydrate 0.58 moles (22.6 g) of the dinitroso derivative prepared in the preceding stage are added portionwise to 930 ml of 96° ethyl alcohol containing 135 ml of water, 11.9 g of ammonium chloride and 390 g of finely powdered zinc and are heated under reflux. At the end of addition the heating is maintained for 1 hour.

Zinc is removed by filtering the reaction mixture hot and the expected product is precipitated by adding 340 ml of a solution of hydrochloric acid in absolute ethanol (7.5 N) to the filtrate. 234 g of expected product are obtained after drying by adding ethyl ether.

Analysis of the product obtained gives the following results:

Analysis for $C_{15}H_{26}N_4O_2Cl_4$

|  | C % | H % | N % | O % | Cl % |
|---|---|---|---|---|---|
| Calculated | 43.53 | 6.53 | 10.68 | 12.21 | 27.05 |
| Found | 43.72 | 6.57 | 10.37 | 12.16 | 27.10 |

EXAMPLE OF PREPARATION 2

Preparation of N,N'-bis($\beta$-hydroxyethyl)-N,N'-bis(4' aminophenyl)ethylenediamine dihydrochloride The procedure followed is as in Example 1, but 1,2-dibromoethane is employed in the first stage instead of 1,3-dichloro-2-propanol.

Analysis for $C_{18}H_{28}N_4O_2Cl_2$

|  | C % | H % | N % | O % | Cl % |
|---|---|---|---|---|---|
| Calculated | 53.60 | 7.00 | 13.89 | 7.93 | 17.58 |
| Found | 53.43 | 6.84 | 13.81 | 8.12 | 17.78 |

EXAMPLE OF PREPARATION 3

Preparation of N,N'-bis(ethyl)-N,N'-bis(4'-amino -3'-methylphenyl)ethylenediamine tetrahydrochloride hydrate 1st stage Preparation of N,N'-bis(ethyl)-N,N'-bis(3' -methylphenyl)-ethylenediamine dihydrochloride The mixture consisting of 1 mole (135.2 g) of N-ethyl-m-toluidine, 60 g of calcium carbonate and 0.55 mole (104 g) of 1,3-dibromoethane is heated for 15 hours under reflux.

After cooling and neutralizing with 60 ml of concentrated hydrochloric acid, followed by extraction with ethyl acetate, the expected product is obtained and is converted into a dihydrochloride with a hydrochloric acid solution in absolute ethanol.

The product is recrystallized from absolute ethanol.

Analysis of the product obtained gives the following results:

Analysis for $C_{20}H_{30}N_2Cl_2$

|  | C % | H % | N % | Cl % |
|---|---|---|---|---|
| Calculated | 65.04 | 8.18 | 7.58 | 19.20 |
| Found | 65.14 | 8.17 | 7.52 | 19.12 |

2nd stage:

Preparation of N,N'-bis(ethyl)-N,N'-bis(3'-methyl -4,'-nitrosophenyl)ethylenediamine A solution of 0.106 moles (7.3 g) of sodium nitrite in 17 ml of water is added dropwise at 0° C. to a solution of 0.05 moles (18.5 g) of N,N'-bis(ethyl)-N,N'-bis(3'-methylphenyl)ethylenediamine in the form of dihydrochloride prepared in the preceding stage, of 20 ml of concentrated hydrochloric acid and 105 g of ice. After the end of addition the stirring is continued for 30 minutes. The hydrochloride of the expected product crystallizes.

The expected product precipitates after addition of 15 ml of 20% strength aqueous ammonia to a suspension of the product obtained in 200 ml of water. Recrystallized from 200 ml of 96° ethanol, it melts at 157° C.

Analysis of the product obtained gives the following results:

Analysis for $C_{20}H_{26}N_4O_2$

|  | C % | H % | N % | O % |
|---|---|---|---|---|
| Calculated | 67.77 | 7.39 | 15.81 | 9.03 |
| Found | 68.03 | 7.42 | 16.06 | 9.16 |

3rd stage:

Preparation of N,N'-bis(ethyl)-N,N'-bis(4'-amino -3'-methylphenyl)ethylenediamine tetrahydrochloride hydrate 0.039 moles (14.1 g) of the dinitroso derivative prepared in the preceding stage are added portionwise to 60 ml of 96° ethyl alcohol containing 8 ml of water, 0.8 g of ammonium chloride and 31 g of finely powdered zinc and heated under reflux. After the end of addition the heating is maintained for 30 minutes.

Zinc is removed by filtering the reaction mixture hot. The expected product is obtained after adding an ethanolic solution of hydrochloric acid and evaporating to dryness.

After purification in an ethanol solution of hydrogen chloride, the product obtained gives the following results:

Analysis for $C_{20}H_{36}N_4OCl_4$

|  | C % | H % | N % | O % | Cl % |
|---|---|---|---|---|---|
| Calculated | 48.99 | 7.40 | 11.43 | 3.26 | 28.92 |
| Found | 48.88 | 7.46 | 11.37 | 3.40 | 28.75 |

EXAMPLES OF DYEING

EXAMPLE 1

The following dye mixture is prepared:

| | |
|---|---|
| N,N'-Bis($\beta$-hydroxyethyl)-N,N'-bis(4'-aminophenyl)-1,3-diamino-2-propanol tetrahydrochloride hydrate | 0.535 g |
| 4-($\beta$-Hydroxyethylamino)-2-hydroxytoluene | 0.418 g |
| meta-Aminophenol | 0.112 g |
| Resorcinol | 0.139 g |
| 4-($\beta$-Hydroxyethoxy)-1,3-phenylenediamine dihydrochloride | 0.05 g |
| Cetylstearyl alcohol sold by Condea under the name Alfol C 16/18 | 8.0 g |
| Sodium cetylstearyl sulphate sold by Henkel under the name Cire de Lanette E | 0.5 g |
| Ethoxylated castor oil sold by Rhône-Poulenc under the name Cemulsol B | 1.0 g |
| Oleyldiethanolamide | 1.5 g |
| Pentasodium salt of diethylenetriaminepentaacetic acid, sold by Protex under the name Masquol DTPA | 2.5 g |
| 22° Bé aqueous ammonia | 11.0 g |
| Water q.s. | 100.0 g |
| pH = 10.1 | |

10 g of 20-volume hydrogen peroxide are added at the time of use. When applied for 20 minutes at 35° C. to 90% naturally white hair, the mixture gives it a slightly purple grey colour after shampooing and rinsing.

EXAMPLE 2

| | |
|---|---|
| N,N'-Bis(β-hydroxyethyl)-N,N'-bis(4'-aminophenyl)ethylenediamine dihydrochloride | 0.72 g |
| N,N'-Bis(ethyl)-N,N'-bis(4'-amino-3'-methylphenyl)ethylenediamine tetrahydrochloride hydrate | 0.70 g |
| 2,4-Diaminophenoxyethanol dihydrochloride | 0.128 g |
| Nonylphenol oxyethylenated with 4 moles of ethylene oxide, sold by Rhône-Pulenc under the name Cemulsol NP 4 | 12.0 g |
| Nonylphenol oxyethylenated with 9 moles of ethylene oxide, sold by Rhône-Poulenc under the name Cemulsol NP 9 | 15.0 g |
| Oleyl alcohol polyglycerolated with 2 moles of glycerol | 1.5 g |
| Oleyl alcohol polyglycerolated with 4 moles of glycerol | 1.5 g |
| Propylene glycol | 6.0 g |
| Ethylenediaminetetraacetic acid sold under the name Trilon B | 0.12 g |
| 22° Bé aqueous ammonia | 11.0 g |
| Water q.s. | 100.0 g |
| pH = 10.1 | |

9 g of 20-volume hydrogen peroxide are added at the time of use. When applied for 25 minutes at 30° C. to permanent-waved hair, the mixture gives it a slightly black blue colour after shampooing and rinsing.

EXAMPLE 3

| | |
|---|---|
| N,N'-Bis(ethyl)-N,N'-bis(4'-amino-3'-methylphenyl)ethylenediamine tetrahydrochloride hydrate | 0.834 g |
| Resorcinol | 0.149 g |
| 2,4-Diaminophenoxyethanol dihydrochloride | 0.399 g |
| 2-Butoxyethanol | 10.0 g |
| Cetylstearyl alcohol sold by Condea under the name Alfol C 16/18 | 8.0 g |
| Sodium cetylstearyl sulphate sold by Henkel under the name Cire de Lanette E | 0.5 g |
| Ethoxylated castor oil sold by Rhône-Poulenc under the name Cemulsol B | 1.0 g |
| Oleyl diethanolamide | 1.5 g |
| Pentasodium salt of diethylenetriaminepentaacetic acid, sold by Protex under the name Masquol DTPA | 2.5 g |
| 22° Bé aqueous ammonia | 11.0 g |
| Water q.s. | 100.0 g |
| pH = 9.6 | |

10 g of 20-volume hydrogen peroxide were added at the time of use. When applied for 20 minutes at 30° C. to bleached hair, the mixture gives it a royal blue colour after shampooing and rinsing.

We claim:

1. N,N'-Bis(β-hydroxyethyl)-N,N'-bis(4'-aminophenyl)-1,3-diamino-2-propanol or one of its addition salts with acids.

2. N,N'-Bis(ethyl)-N,N'-bis(4'-amino -3'-methylphenyl)-ethylenediamine or one of its addition salts with acids.

3. A composition for dyeing keratinous fibres, in particular for hair, comprising, an effective concentration of an oxidation dye precursor selected from the group consisting of N,N'-bis(β-hydroxyethyl) -N,N'-bis (4'-aminoinophenyl)-1,3-diamino -2-propanol, N,N'-bis-(ethyl)-N,N-40 -bis (4'-amino-3'-methylphenyl)ehtylenediamine, acid addition salts of N,N'-bis(β-hydroxyethyl) -N,N'-bis (4'-amino-phenyl)-1,3-diamino -2-propanol and N,N'-bis(ethyl)-N,N'-bis(4'-amino-3'-methylphenyl) ethylenediamine and a carrier suitable for dyeing said fibres, wherein said effective concentration is sufficient, upon oxidative coupling of said precursor, to dye said fibres.

4. The composition fo claim 3, further comprising at least one coupler, wheein said couplers are selected from the group consisting of couplers that, in the presence of an oxidizing agent, react with said precursors to form dyes and wherein the concentration of said couplers is sufficient for formation of said dye, and wherein said couplers are selected from the group consisting of phenols, meta-diphenols, meta-phenylenediamines, meta-aminophenols, heterocyclic couplers derived from pyridine, sesamol and its derivatives, mono- or polyhydroxylated derivatives of naphthalene and of aminonaphthaline, pyrazolones and benzomorpholines.

5. The composition of claim 3, wherein said effective concentration is between 0.05 and 12% by weight relative to the total weight of the composition.

6. The composition of claim 3, said carrier is water which has an alkaline pH.

7. The composition of claim 4, wherein the concentration of said couplers is between 0.05 and 10% by weight relative to the total weight of the composition.

8. A process for dyeing keratinous fibres, comprising applying an effective amount of the composition of claim 3 to said fibres in the presence of an oxidizing solution.

* * * * *